United States Patent [19]

Hetrick et al.

[11] 4,272,329
[45] Jun. 9, 1981

[54] STEADY STATE MODE OXYGEN SENSOR AND METHOD

[75] Inventors: Robert E. Hetrick, Dearborn Heights; William A. Fate, Ann Arbor, both of Mich.

[73] Assignee: Ford Motor Company, Dearborn, Mich.

[21] Appl. No.: 126,606

[22] Filed: Mar. 3, 1980

[51] Int. Cl.³ .......................................... G01N 27/58
[52] U.S. Cl. .................................. 204/1 T; 204/195 S
[58] Field of Search ...................... 204/195 S, 1 S; 123/438, 489; 324/71 R

[56] References Cited

U.S. PATENT DOCUMENTS

| | | | |
|---|---|---|---|
| 3,514,377 | 5/1970 | Spacil et al. | 204/1 T |
| 3,562,521 | 2/1971 | Vanderschmidt et al. | 250/43.5 |
| 3,699,032 | 10/1972 | Rapp | 204/195 S |
| 3,738,341 | 6/1973 | Loos | 123/119 R |
| 3,948,081 | 4/1976 | Wessel et al. | 73/23 |
| 4,066,528 | 1/1978 | Mansfield | 204/195 T |
| 4,111,776 | 9/1978 | Mansfield | 204/195 T |
| 4,112,893 | 9/1978 | Anzai | 123/119 EC |
| 4,158,166 | 6/1979 | Isenberg | 324/29 |
| 4,169,440 | 10/1979 | Taplin et al. | 123/119 EC |

Primary Examiner—G. L. Kaplan
Attorney, Agent, or Firm—Peter Abolins; Clifford L. Sadler

[57] ABSTRACT

This specification discloses a device to determine the percentage of oxygen in an ambient atmosphere. The device, which is immersed in the atmosphere, is constructed to define an enclosed volume in which the atmosphere can be established by means of a small leak. The enclosing structure contains two partitions which can conduct oxygen ions and act as electrochemical cells. One partition is called the pump cell while the other is called the sensor cell. When attached to an external power supply, the current ($I_p$) drawn through the pump cell either adds or removes (from or to the ambient) gaseous oxygen from the volume. As a result of the pumping action, an EMF ($V_S$) develops across the sensor cell which can be used to measure the change in oxygen partial pressure in the volume relative to the ambient. If an external circuit causes adequate current to flow in the pump cell to keep the sensor EMF at a constant value, then the magnitude of the current is linearly proportional to the percentage of oxygen in the atmosphere.

10 Claims, 8 Drawing Figures

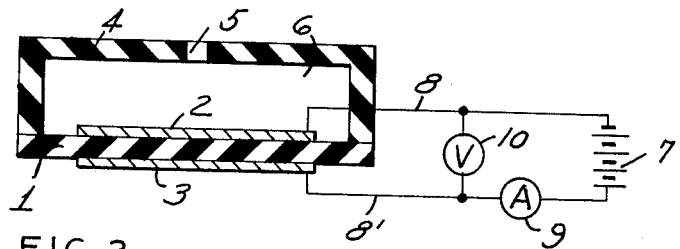
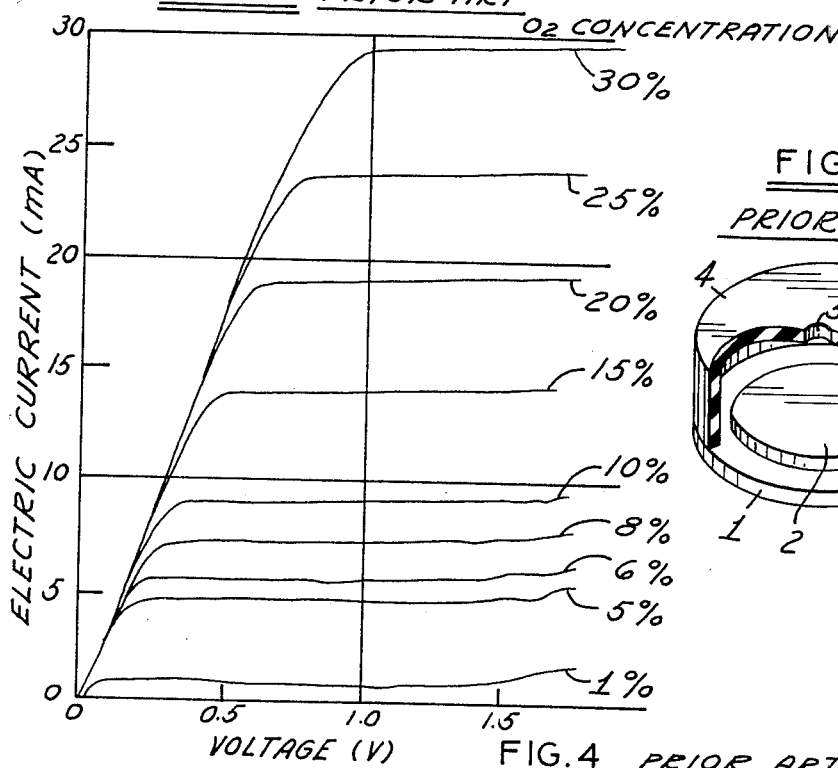
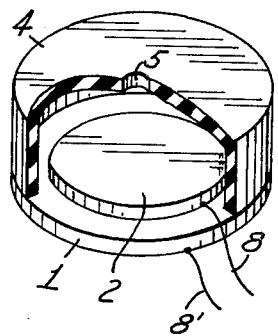
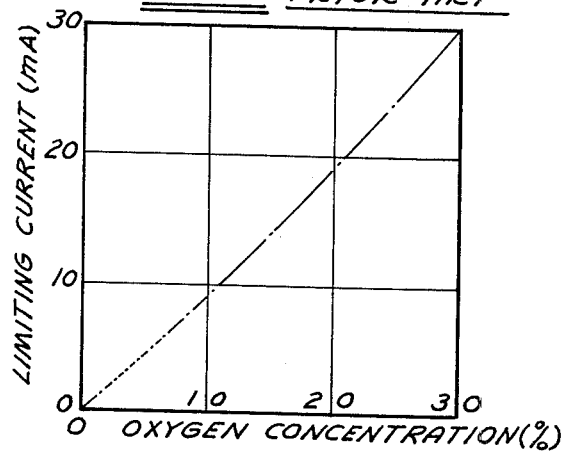

STEADY STATE MODE OXYGEN SENSOR AND METHOD

BACKGROUND OF THE INVENTION

1. Field of the Invention

This invention relates to determining the concentration of oxygen in a gaseous atmosphere.

2. Prior Art

U.S. Pat. Nos. 3,907,657 to Heijne and 3,514,377 to Spacil et al relate to the measurement of oxygen ($O_2$) concentrations using solid electrochemical devices. For applications at elevated temperatures (>500° C.), for example, as might be encountered in the exhaust gases of furnaces or automobiles, the active material in these devices may be ceramic zirconium dioxide suitably adapted for the conduction of $O^=$ ions. Electrochemical cells made from this material are suitable at elevated temperatures for oxygen sensing and pumping applications.

The mode of operation of the Heijne device can be described as an oxygen counting mode in which oxygen partial pressure is determined on a sampling basis. A constant current (or equivalent means) is applied to an electrochemical cell which forms part of the enclosure of a volume for a period of time, $t_p$, for the purpose of electrochemically pumping out most of the oxygen from that volume. The ambient atmosphere had established itself within the volume prior to the pump out, by means of a leak. An additional electrochemical cell, which serves as a sensor of the reduced oxygen partial pressure within the volume and which also constitutes a portion of the enclosure, provides a signal indicating when oxygen has been sufficiently depleted from the volume (see FIG. 4 of Heijne). Knowing the temperature, enclosed volume and the pump out current and time allows one to calculate the number of oxygen molecules within the enclosure from the ideal gas law. The number of oxygen molecules is in turn proportional to the desired oxygen partial pressure. If a constant pump current is used, the pump out time $t_p$ is proportional to the oxygen partial pressure. If a constant current is not used, then the integral of the pump out current over the pump out time is proportional to the oxygen partial pressure.

The Heijne device can provide an output which is linearly proportional to the oxygen partial pressure. This is superior, for example, to single oxygen concentration cells used as sensors which give an output (EMF) proportional to the natural logarithm of the oxygen partial pressure ln ($p_{O_2}$).

A potential disadvantage of the Heijne device is response time. For this measurement procedure, the leak connecting the ambient to the enclosed volume must be small so that during the pump out of oxygen, no significant amount of oxygen leaks into the volume to cause an error in the count of molecules (i.e., to erroneously increase $t_p$). However, if the leak is made small, it may take a long time, $t_v$, for the ambient to reestablish itself with the volume after a pump out. If the changes in the oxygen partial pressure in the ambient occur rapidly with respect to this refill time, the device would not be able to follow these changes in repetitive operation.

U.S. Pat. Nos. 3,923,624 to Beckmans et al, 3,654,112 to Beckmans et al, and 3,907,657 to Heijne et al describe tubular ceramic structures for measuring and controlling the composition of oxygen in a carrier gas. In some cases a pump cell and a sensor cell are used. U.S. Pat. Nos. 3,923,624 and 3,654,112 teach devices to be used primarily to dose a gas with oxygen to a constant partial pressure. Measurement of the dosed gas is made by a standard technique using a zirconium dioxide oxygen concentration cell to be sure that the dosed gas contains the correct amount of oxygen. The sensitivity of the concentration cell to the oxygen partial pressure is low, being proportional to ln ($P_{O_2}$). This purpose is divergent from the purpose of measuring with high sensitivity the oxygen partial pressure in a feedgas as would be required in an automotive application. There is no suggested application of these devices for an auto exhaust application.

In the case of the teachings of U.S. Pat. No. 3,698,384 to Jones, the purpose is to measure oxygen partial pressure in a feedgas. This is done by measuring an electrochemical cell pumping current while holding the sensor cell voltage a constant. However, to achieve a result in the disclosed open ended tubular structure made from zirconium dioxide the flow rate of the feedgas must be kept constant. If the flow rate should attempt to vary, there is a relatively elaborate flow control circuit to keep the flow rate a constant. This scheme, which also employs a reference atmosphere is relatively unsuitable for application in an auto exhaust where the exhaust flow rate would change substantially with RPM.

U.S. Pat. Nos. 3,347,735 to McKee and 3,857,771 to Sternberg both describe oxygen sensing procedures or devices wherein the taking of a first derivative of an output signal either determines the oxygen partial pressure or can yield information on the medium which contains the oxygen. Neither device would be suitable for the continuous or repeated determination of the oxygen partial pressure in a variable, high temperature environment like that occurring in an automotive exhaust. U.S. Pat. Nos. 3,948,081; 3,738,341 and 4,112,893 relate to oxygen sensors and associated electrical circuitry which are a typical oxygen concentration cell type. These patents discuss external circuitry which may enhance the operation of such sensors under various conditions.

FIGS. 1 and 2 of the drawings illustrate a known oxygen pumping sensor in which ionically conducting zirconium dioxide material 1 with thin platinum electrodes 2 and 3 form an electrochemical cell which with additional ceramic structure 4 defines an enclosed volume 6. The ambient atmosphere can establish itself within the volume by means of a leak opening 5. A battery 7 is attached to the electrodes by means of lead wires 8 and 8'. A voltmeter 10 and ammeter 9 are provided to determine the voltage drop across the pump cell and the current flowing through it. Although similar to structure to FIG. 5 of U.S. Pat. No. 3,907,657, the operation is different. Here one applies a pump voltage V to remove oxygen from an enclosed volume 6 until the pump current saturates. The saturated current is proportional to oxygen partial pressure or concentration. This saturation property is shown in FIGS. 3 and 4.

This is a steady-state device. When steady state is reached, the flow of oxygen through leak opening 5 equals the pump current times a proportionality constant. The current saturates at a voltage greater than about 0.5 V because the leak in combination with the platinum electrode 2, the cathode, will only allow a limited (saturated) amount of oxygen to enter and be electrochemically pumped from the volume per unit time. The device has the advantage of giving an output signal (the value of the limiting current) which is linearly proportional to the desired ambient the oxygen partial pressure. However, to the extent that the saturated current value depends on the detailed properties of the electrode 2, the device calibration may be subject to drift as these detailed properties may change during the sintering and wear of this thin layer.

An important application of high temperature oxygen sensors is in the determination of the stoichiometric air fuel mixture in the exhaust gases of hydrocarbon fired furnaces or engines such as automobile internal combustion engines. The stoichiometric mixture is one in which the mass of air present contains just enough oxygen to react with the mass of hydrocarbons present so that there is the minimum amount of both oxygen and hydrocarbons remaining. For common automotive gasoline, the air fuel ratio A/F=mass of air/mass of fuel) at the stoichiometric point is approximately 14.6. If, for example, an engine were running lean of stoichiometry (A/F 14.6) there would be an excess of air in the "charge" burned in the cylinder of an internal combustion engine and the exhaust gas would contain a substantial oxygen partial pressure. If rich operation were occurring, e.g., an air fuel ratio less than 14.6, the exhaust gas would contain unreacted or partially reacted hydrocarbons and very low oxygen partial pressure. In particular, the equilibrium oxygen partial pressure in the exhaust gas can change by a great amount (as much as 20 orders of magnitude) as one moves from lean to rich operation. This large change forms the basis for detecting the stoichiometric air fuel ratio with an exhaust gas oxygen sensor. The electrical output of such a sensor can then be fed back to an electrically controllable carburetor or fuel injection system for maintaining engine operation always at the stoichiometric point. Depending on engine type operation at this point frequently offers a reasonable compromise for minimizing regulated exhaust gas emissions and maximizing engine performance.

There are known high temperature oxygen sensors utilizing oxygen electrochemical concentration cells (usually made from zirconium oxide) and requiring the use of a reference atmosphere (usually air) which are suitable for determining the stoichiometric air fuel ratio in a high temperature automotive environment. These devices give an output (EMF) proportional to the natural logarithm of the oxygen partial pressure. Despite their low sensitivity to oxygen partial pressure, the large change in oxygen partial pressure at the stoichiometric point allows their useful implementation.

For some engines it is useful to operate lean of the stoichiometric A/F for the purpose of reducing fuel consumption. Oxygen partial pressure varies in a systematic way in the lean region and this can form the basis for determining lean A/F. The exact knowledge of lean A/F would be useful to fully implement a lean burn engine strategy which would maximize fuel economy and engine performance and minimize regulated emissions. However, the variation in oxygen partial pressure in the appropriate lean A/F region, e.g., air fuel ratio is greater than 16 and less than 20, is not large, (in comparison to the changes occurring near stoichiometry) so that suitable oxygen sensors with sensitivities greater than the natural logarithm of oxygen partial pressure are desirable for accurate measurement in the desired A/F range. These are some of the problems this invention overcomes.

SUMMARY OF THE INVENTION

In accordance with an embodiment of this invention, a ceramic electrochemical structure with associated external circuitry is capable of measuring oxygen concentration in a high temperature surrounding environment such as may be found in an automotive exhaust. The external circuitry provides an electrical output whose magnitude is proportional to the percentage of gaseous oxygen. The structure includes two oxygen ion ($O=$) conducting electrochemical cells, a pump cell and a sensor cell, which in part provide the enclosing structure of a nearly enclosed volume. A portion of the remaining structure can be a hollow ceramic tube. The cells are attached to the end faces of the tube. A small aperture in the enclosing structure allows the ambient atmosphere, containing oxygen in a percentage to be determined, to leak into the volume.

In operation, the external circuitry causes a voltage to be applied to the pump cell with a proper polarity to electrochemically pump oxygen out of the volume and return it to the ambient. After a brief transient period, a steady state is reached where the rate at which oxygen is pumped from the volume is equalled by the rate at which oxygen is diffusing into the volume by means of the aperture. Under this steady-state condition, the oxygen partial pressure within the volume is reduced from that in the ambient causing an EMF to develop across the electrodes of the sensor cell. Experimentally, it is found that if one causes the pump cell current to be continuously adjusted so that the sensor cell EMF is always a constant (a task which can be done automatically with a simple "servo circuit"), then the magnitude of the pump cell current is linearly proportional to the percentage of oxygen in the ambient atmosphere. This linear relationship is the basis of sensor operation.

Besides the high sensitivity to oxygen concentration, a further advantage of this sensing technique is that it is proportional to the percentage of oxygen in the ambient rather than oxygen partial pressure. The latter of course varies linearly with total pressure while the former does not. Accordingly, one can obtain an unambiguous measure of oxygen content in the ambient even under conditions where the total pressure may be changing. In an automotive application such changes could occur due to different atmospheric conditions or a change in altitude. A further advantage is that the device yields a continuous output which, in general, does not require as much ancillary electronic circuitry as for pulsed or repetitive mode devices.

BRIEF DESCRIPTION OF THE DRAWINGS

FIGS. 1 through 4 are prior art drawings with FIGS. 1 and 2 showing the construction of an electrochemical oxygen pumping device and FIGS. 3 and 4 show graphical representation of characteristics of the device;

DETAILED DESCRIPTION OF THE INVENTION

This disclosure teaches a solid electrochemical device, attached circuitry and a measurement technique for measuring the percentage or fractional content of oxygen in a high temperature gaseous environment such as may be found in an automotive exhaust. In the latter environment, as an example, the electrical output of the device, which is proportional to the desired oxygen percentage, may be used in the feedback control of the air-to-fuel ratio of the automotive engine especially under lean operating conditions.

Figure 5A:
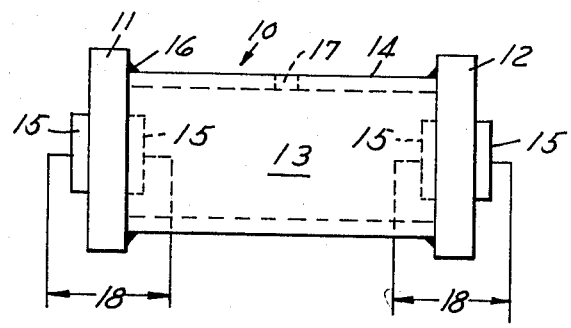
FIG. 5a is a schematic diagram of a portion of a device in accordance with an embodiment of this invention.
Figure 5B:
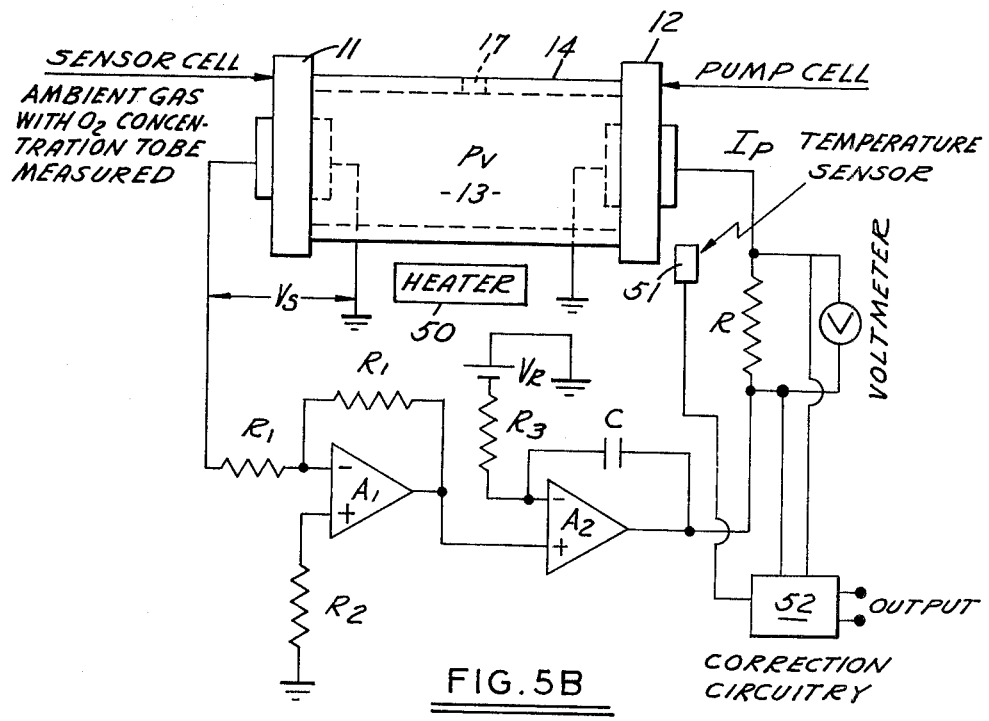
FIG. 5b is a schematic diagram similar to FIG. 5a with the addition of external circuitry for the measurement of oxygen percentage in an ambient gas.

As shown in the embodiment of FIGS. 5a and 5b, the device 10 includes two platelets, 11 and 12, of zirconium dioxide suitably adapted for the conduction of $O^=$ ions. Such a solid ionic conductor is called a solid electrolyte. Electrodes 15 are attached to opposing faces of each platelet to form electrochemical cells. The right hand cell is termed the pump cell and the left hand cell the sensor cell to reflect their functions. The electrodes consist of platinum films (typically applied by common sputtering techniques) with a typical thickness of 1.0 micron, or other material adapted for the purpose. Lead wires 18 are affixed to each electrode so that external circuitry may be applied to the cells. Using glass frits or ceramic glue 16, the zirconium dioxide platelets are joined by a hollow, non-porous ceramic tube 14 to define an enclosed volume 13. The joining is effected so that one electrode from each cell will lie within the enclosed volume. A small hole 17 can be drilled into the ceramic tube to allow the ambient atmosphere to establish itself within the volume. Alternatively, the seals between the zirconium dioxide and the tube can be made somewhat leaky for the same purpose. The cells must be operated at an elevated temperature ($\gtrsim 500°$ C.) so that the electrolyte is suitably conducting. Other embodiments may incorporate other $O^=$ conducting solid electrolytes (ex. $CeO_2$ adapted for the purpose) which can perform the desired electrochemical functions at lower temperatures. The device is completely immersed in the atmosphere whose percentage of oxygen is to be determined.

Electrical operation can be discussed with reference to FIG. 5b which shows the device wired to an external circuit. The circuitry is of simple servo feedback nature in which an amplifier $A_2$ produces an output voltage and current which causes oxygen to be electrochemically pumped from the enclosed volume by the action of the pump cell. A known resistor R is in series with the pump cells so that the magnitude of the pump current ($I_p$) can be determined by measuring the voltage across R. After an initial transient period, a steady state is reached where the number of oxygen molecules removed by pumping is equalled by a flux ($I_L$) of oxygen molecules diffusing into the volume by means of the aperture in the connecting tube. The oxygen is diffusing through whatever gaseous species, the carrier gas, comprises the remainder of the ambient atmosphere. This equality is expressed by Eq. (1)

$$I_L(O_2 \text{molecules/sec}) = (I_P/4e) (O_2 \text{ molecules/sec}) \quad (1)$$

where e is the electronic charge and 4e converts $I_P$ in amps to an equivalent number of oxygen molecules/sec. At steady state $P_V$, the oxygen partial pressure which is assumed to be constant throughout the enclosed volume, adopts a value less than $P_A$, the oxygen partial pressure in the surrounding ambient. As a result of this partial pressure difference, an electromotive force, labelled $V_S$, will develop across the sensor cell of a magnitude given by the familiar Nernst equation as shown in Eq. (2).

$$V_S = (RT/4F) \ln (P_A/P_V) \quad (2)$$

where T is the absolute temperature and R and F are the ideal gas and Faraday constants, respectively.

The essential feature allowing the use of the device as a sensor is the observation that $I_P$ is related to $P_V$ as shown in Eq. (3).

$$I_P = \sigma_L(P_A - P_V) \quad (3)$$

where $\sigma_L$ is a constant characterizing the leak conductance. This relation as well as the magnitude of $\sigma_L$ are established by varying $I_P$ while using calibrated gases to set $P_A$, and measuring $V_S$ which through Eq. (2) allows one to compute $P_V$. The constant $\sigma_L$ is found to increase with T, the area of the leakage aperture, and the chemical nature of the carrier gas (e.g., $N_2$ or $CO_2$), and to be inversely proportional to the absolute pressure P in a manner indicating that oxygen is leaking into the volume by the gaseous diffusion mechanism. If one now solves Eq. (2) for $P_V$ and substitutes the result in Eq. (3) one finds $$I_P = P_A \sigma_L (1 - \exp(-4FV_S/RT)) \quad (4)$$

If the gases involved obey the ideal gas law, which is an excellent approximation at the elevated temperatures of interest, then $P_A = \alpha P$ where $\alpha$ is the fractional number of molecules in the ambient atmosphere that are oxygen. Accordingly, if $\beta = 100\% \times \beta$ then $\beta$ is the percentage of oxygen in the ambient. Further since $\sigma_L \sim (1/P)$ one has the result that $$I_P \sim \beta f(V_S, T), \quad (5)$$

where $f(V_S, T)$ is a function of $V_S$ and T, so that if $V_S$ and T are held constant, $I_P$ is linearly proportional to the percentage of oxygen in the ambient. A heater 50 or other suitable means can be used to maintain T at a constant value while the remainder of the circuitry in FIG. 5b acts to maintain $V_S$ at a constant value by continually adjusting the value of $I_P$ as required. This is done by applying $V_S$ to the amplifier $A_1$, which in combination with suitable resistors $R_1$ and $R_2$ can be used as an inverting, unity-gain, buffer amplifier whose output ($= -V_S$) is applied to the positive input of amplifier $A_2$. $A_2$ in turn produces an output proportional to the difference between $-V_S$ and an adjustable reference voltage $V_R$. The polarities are chosen so that the changes in the output current ($I_P$) act to reduce the difference between $-V_S$ and $V_R$. Resistor $R_3$ and capacitor C are chosen appropriately to damp out the effects of very sudden oxygen percentage changes and to prevent oscillations which are common in undamped servo feedback circuits. Numerous other circuits can be devised as required to perform the identical control function.

In use, the proportionality constant between $I_P$ and $\beta$ could be determined using calibrated gases. With this constant, the voltage across R would serve to specify $I_P$ and hence the percentage of oxygen. The proportionality constant varies somewhat with the nature of the carrier gas. Accordingly, large variations in the composition of the carrier gas would have to be accounted for in accurate measurements.

Figure 6:
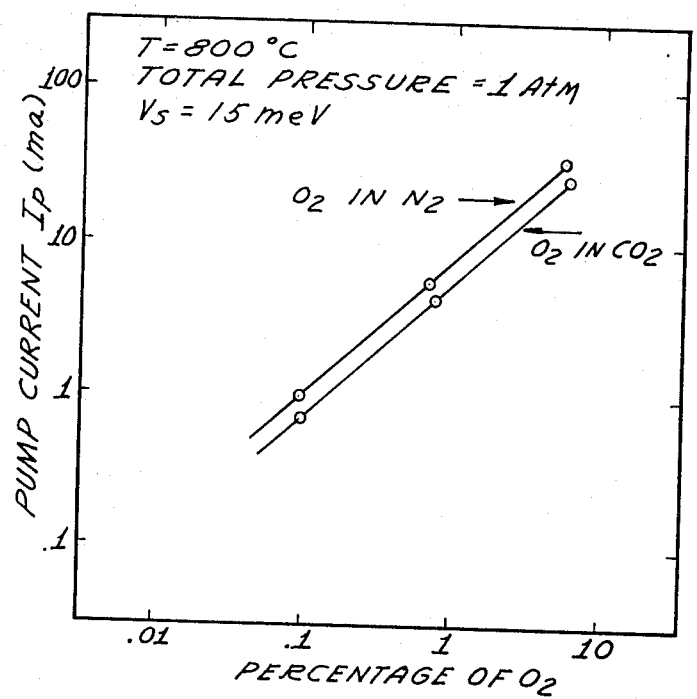
FIG. 6 is a graphical representation of the pump cell current plotted against the percentage of oxygen in two different carrier gases at one atmosphere total pressure.
Figure 7:
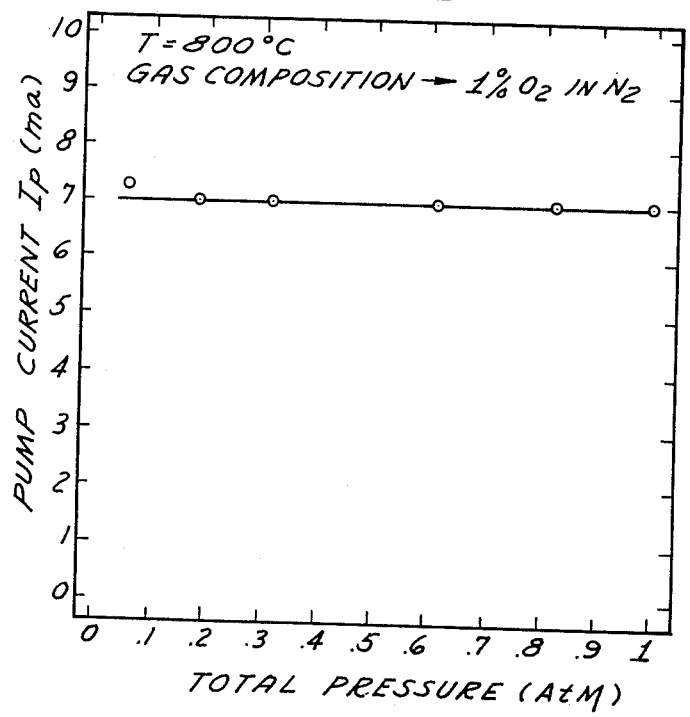
FIG. 7 is a graphical representation of pump cell current plotted against total pressure for a gas containing 1% oxygen in nitrogen at a temperature of 800° C.

FIG. 6 shows a graphical representation of the results for a particular device operated at T=800° C. $I_P$ is plotted on a logarithmic scale on the vertical axis while oxygen percentage is plotted on a logarithmic scale on the horizontal axis. The linear dependence is evidenced along with the variation observed for different carrier gases. The total pressure of the gases was one atmosphere for all measurements. FIG. 7 shows a graphical representation of $I_P$ plotted against the total atmospheric pressure for a gas containing 1% oxygen in $N_2$ at T=800° C. The result shows the independence of $I_P$ on total pressure in this range.

An advantageous aspect of this mode of oxygen measurement is the weak temperature dependence of the sensed parameter, $I_P$. This arises because $\sigma_L$ in Eq. (4) is an increasing function of T while the right hand factor of $\sigma_L$ is a decreasing function of T. For a given application, a near cancellation of the temperature dependence over an approximate 100° C. temperature range can be achieved by a judicious choice of $V_S$. This feature relaxes the performance requirements of any heater assembly which would be necessary in conjunction with the device to maintain the temperature constant within an acceptable range.

To facilitate accuracy, it may be advantageous to account for the effects of changes in the temperature of the ambient atmosphere. This can be done in two ways. Firstly, referring to FIG. 5b, a heater 50 is used to maintain the temperature of device 10 and its adjacent gaseous surroundings within a sufficiently narrow range of values that a predetermined accuracy of the oxygen percentage measurement can be maintained with a single calibration constant appropriate for that narrow range of temperatures. As a given application requires, the "heater" may need to include a more elaborate electrical heating system in which a temperature sensor in the vicinity of the device, such as a thermocouple, provides the input to an electrical temperature regulator whose output activates the heater to a variable degree sufficient to maintain the temperature sensor output (or equivalently, the temperature) equal to some constant reference value preset in the regulator. Alternately a temperature sensor 51 may be used to form one input of temperature correction circuitry 52 whose other input is $I_P$. The purpose of the circuitry is to correct $I_P$ for the changes in the device calibration constant resulting from changes in the temperature. The output of the circuitry can be a convenient electrical quantity, such as a voltage, whose magnitude is proportional to oxygen percentage regardless of temperature. Depending on the application, the correction circuitry may need to encompass the facilities of a small computer.

Similar results are obtained if the polarities of the reference batteries and amplifiers are modified so that the output of amplifier $A_2$ causes a pump cell current which injects oxygen from the ambient into the enclosed volume.

Various modifications and variations will no doubt occur to those skilled in the various arts to which this invention performs. For example, the electrodes may vary in shape from those described herein. These and all other variations which basically rely on the teachings through which this disclosure has advanced the art are properly considered within the scope of this invention.

What is claimed is:

1. An electrochemical apparatus for making a measurement of oxygen partial pressure in an ambient environment including other gaseous materials, said electrochemical apparatus including:
    a solid electrochemical pump cell;
    a solid electrochemical sensor cell;
    an associated supporting structure which in combination with said pump and sensor cells defines an enclosed volume;
    a leak orifice for providing communication between said enclosed volume and the ambient environment so that when said enclosed volume is immersed in an ambient environment containing a partial pressure of oxygen there is a tendency for the partial pressure of oxygen inside said enclosed volume to equalize with the partial pressure of oxygen of the ambient environment;
    an external circuit means coupled to said pump cell to apply an electrical input to said pump cell and coupled to said sensor cell for measuring an electrical output generated by said sensor cell in response to said electrical input at said pump cell, said external circuit means including a control means to apply a current of sufficient magnitude as said electrical input to maintain a constant voltage across said sensor cell, and said external circuit means including sensing means for sensing the magnitude of said electrical input which is proportional to the percentage of oxygen in the ambient environment thus permitting said electrochemical apparatus to be used as a sensor of the percentage of oxygen;
    said pump and sensor cells being formed of platelets of solid ionic conductors capable of conducting oxygen ions, and including two electrode layers attached to opposing faces of each of said platelets, and lead wire attached to each of said electrodes for coupling said first and second circuit means to said pump and sensor cells, respectively.

2. An electrochemical apparatus as recited in claim 1 wherein:
    said external circuit means includes servo feedback means having an output which causes a current to pass in said electrochemical pump cell so that oxygen is electrochemically pumped from said enclosed volume and an EMF is caused to develop across said electrochemical sensor cell, said EMF providing an input for said external circuit means, said external circuit means being adapted to produce an output current which will keep the magnitude of the EMF at said electrochemical sensor cell constant at a desired value; and
    said external circuit means further includes a series resistor for passing the current to said electrochemical pump cell and measuring means for measuring the voltage across said series resistor.

3. An electrochemical apparatus as recited in claim 1 wherein:
    said associated supporting structure includes a hollow tube of material which is impervious to gases and retains a structural rigidity at elevated temperatures found in the exhaust gases of an internal combustion engine; and
    said pump cell and said sensor cell being affixed to opposing ends of said tube by a mounting means;
    said pump and sensor cells being affixed to said tube so that one of said electrodes of each of said cells forms a part of the surface adjacent said enclosed volume.

4. An electrochemical apparatus as recited in claim 1 further comprising a heater to maintain the temperature of said electrochemical structure and its adjacent gaseous surroundings so that a single calibration constant appropriate for the maintained range of temperatures can be used.

5. An electrochemical apparatus as recited in claim 1 further comprising:
a correction circuit means coupled to said external circuit means for measuring the temperature in the region of said sensor cell and for correcting said electrical input applied to said pump cell for variations in temperature.

6. An electrochemical apparatus as recited in claim 1 wherein said external circuit means is adapted to apply an electrical input to said pump cell causing oxygen to be pumped into said enclosed volume and maintaining a generated EMF across said sensor cell at a constant value so that said electrical input of said pump cell provides a measure of the percentage of oxygen in the ambient environment.

7. A method for making a measurement of oxygen partial pressure in an ambient environment having other gaseous material including the steps of:
establishing an enclosed volume with restricted access to the ambient environment, the enclosed volume being bounded by a solid electralyte electrochemical pump cell and a solid electrolyte electrochemical sensor cell, and the restricted access being sufficient so that when the enclosed volume is immersed in an ambient environment containing a partial pressure of oxygen there is a tendency for the partial pressure of oxygen inside the enclosed volume to equalize with the partial pressure of oxygen of the ambient environment;
applying to the pump cell an electrical current of sufficient magnitude to maintain a constant voltage across the sensor cell so that the magnitude of the electrical input is proportional to the percentage of oxygen in the ambient environment thus determining the percentage of oxygen;
measuring the magnitude of the current drawn through the pump cell;
measuring an electrical output generated by the sensor cell in response to the electrical input at the pump cell; and
calculating the oxygen percentage using a proportionality with the input current to the pump cell.

8. A method as recited in claim 7 further comprising the step of:
applying the electrical input to the pump cell so that oxygen is pumped into said enclosed volume.

9. A method as recited in claim 8 further comprising the step of:
maintaining the temperature of the enclosed volume and adjacent regions so that a single calibration constant appropriate for the maintained range of temperatures can be used.

10. A method as recited in claim 8 further comprising the step of:
measuring the temperature in the region of the sensor cell and correcting the measurement of the oxygen percentage for the dependence of the temperature measuring output on the temperature.

* * * * *